US008916728B2

(12) United States Patent
Ruppin et al.

(10) Patent No.: US 8,916,728 B2
(45) Date of Patent: Dec. 23, 2014

(54) PROCESS FOR PREPARING ALKYLALKANOLAMINES

(75) Inventors: Christophe Ruppin, Saint-Pierre d'Albigny (FR); François Guillemet, Paris (FR)

(73) Assignee: Arkema France, Colombes Cedex (FR)

( * ) Notice: Subject to any disclaimer, the term of this patent is extended or adjusted under 35 U.S.C. 154(b) by 110 days.

(21) Appl. No.: 13/379,187

(22) PCT Filed: Jun. 25, 2010

(86) PCT No.: PCT/FR2010/051299

§ 371 (c)(1), (2), (4) Date: Jan. 23, 2012

(87) PCT Pub. No.: WO2010/149936

PCT Pub. Date: Dec. 29, 2010

(65) Prior Publication Data

US 2012/0116126 A1 May 10, 2012

(30) Foreign Application Priority Data

Jun. 25, 2009 (FR) ...................................... 09 54334

(51) Int. Cl.

*C07C 213/02* (2006.01)
*C07C 213/10* (2006.01)
*C07C 213/00* (2006.01)
*C07C 217/00* (2006.01)

(52) U.S. Cl.

CPC ............. *C07C 213/00* (2013.01); *C07C 217/00* (2013.01)
USPC ............................ 564/473; 564/472; 560/265

(58) Field of Classification Search

CPC ............................ C07C 213/00; C07C 217/00
USPC .................................................. 564/472, 473
See application file for complete search history.

(56) References Cited

U.S. PATENT DOCUMENTS 2,600,301 A * 6/1952 Kerwin et al. ................ 564/381
3,457,313 A * 7/1969 Baker ........................... 564/473
4,190,601 A 2/1980 Decker
4,521,624 A * 6/1985 Jackisch ....................... 564/446
8,420,864 B2 * 4/2013 Ruppin et al. ................ 564/473

FOREIGN PATENT DOCUMENTS

CN 101492380 A * 7/2009
JP 2009-173553 8/2009

OTHER PUBLICATIONS

Kumpaty et al. Selective Access to Secondary Amines by a Highly Controlled Reductive Mono-N-Alkylation of Primary Amines. Synthesis 2003, 14, 2206-2210.*
Zhao, Z. "Process for producing miglitol key intermediate" CN 101492380A English Machine Translation obtained from Espacenet online [Jul. 15, 2014].*
International Search Report received in PCT/FR2010/051299, mailed Sep. 30, 2010.

* cited by examiner

*Primary Examiner* — Samantha Shterengarts
*Assistant Examiner* — Amanda L Aguirre
(74) *Attorney, Agent, or Firm* — Smith, Gambrell & Russell, LLP

(57) ABSTRACT

The present invention relates to a process for preparing alkylalkanolamines, comprising the reaction of a carbonyl-based compound with a hydroxylalkylamine, in the presence of hydrogen and a catalyst.

18 Claims, No Drawings

PROCESS FOR PREPARING ALKYLALKANOLAMINES

The present invention relates to a process for the synthesis of alkylalkanolamines (subsequently referred to as AAAs), in particular an improved process for obtaining, in particular at the industrial level, alkylalkanolamines of high purity, with high yields, without the use of raw materials of epoxide type.

AAAs, and in particular alkylethanolamines, are intermediate compounds which are important in the chemical industry and in the pharmaceutical industry, where they can be used as dispersing agents, emulsifiers or surfactants or in the synthesis of active ingredients. They are also used as a neutralizing agent in water-based paints, or as a corrosion inhibitor in lubricants or hydraulic fluids, to cite only the most common applications.

According to the mode of preparation commonly used, AAAs, and in particular alkylethanolamines, are obtained by reacting primary or secondary amines with an epoxide, respectively ethylene oxide, as indicated in the reaction below:

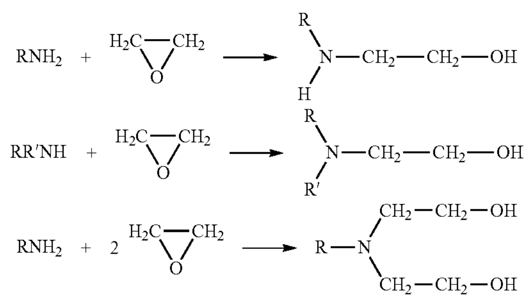

These reactions are, for example, described in patent applications FR 2 251 545 (BASF) or else FR 2 387 212 (Bayer).

According to this reaction scheme, the secondary amines thus result in N,N-dialkylethanolamines, while the primary amines result in N-alkylethanolamines or in N-alkyldiethanolamines depending on the stoichiometric ratio used.

However, and in particular in the case of primary amines, the reaction most commonly results in a mixture of alkylmonoethanolamine and alkyldiethanolamines which are sometimes difficult to separate depending on the nature of the alkyl group.

Moreover, this preparation mode results in by-products which are compounds from polyaddition of the epoxide used, for example when ethylene oxide is used:

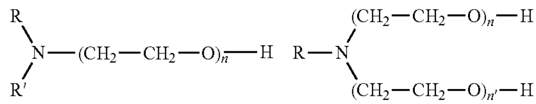

It is also well known that proceeding in this manner results in AAAs, in particular alkylethanolamines, which become colored during distillation and/or during storage. This coloration is due to the presence of conjugated unsaturated impurities and/or of carbonylated derivatives and can prove to be particularly bothersome for certain applications, in particular in paints (white bases).

Various treatment methods have been described for limiting this problem of alkylethanolamine coloration.

Among these, mention may be made of those described in patents and patent applications US 2004/0110988 (Air Products), U.S. Pat. No. 6,291,715 (BASF), EP 632013 (Union Carbide) and EP 477593 (Atochem), to cite just some of them, and in order to show the large number of studies carried out in order to attempt to find a solution to this coloration problem.

In particular, in order to inhibit the compounds capable of introducing a coloration, one solution consists in treating the reaction crude, or the previously distilled AAA, with a reducing agent (such as hydrogen, $NaBH_4$, and the like). This solution therefore requires an additional treatment of the reaction crude, which can prove to be expensive in terms of energy expended and loss of yield.

There remains therefore, at this time, a need for a process for the synthesis of AAAs, which can be readily industrialized, which has good yields, which can do without the use of raw materials that are dangerous or difficult to use, and which generates only few or no by-products, in particular by-products responsible for the coloration of AAAs.

These objectives are totally or at least partly achieved by virtue of the present invention, details of which are given in the description which follows.

Thus, according to a first aspect, the subject of the present invention consists of a direct synthesis process which avoids handling compounds bearing an epoxide function, in particular ethylene oxide, which is an extremely inflammable and toxic liquefied gas, said direct synthesis process, after distillation, resulting in AAAs, in particular alkylethanolamines, of high purity which are colorless and storage-stable, without any additional specific purification treatment.

More specifically, the present invention relates to the process for preparing alkylalkanolamines of formula (A):

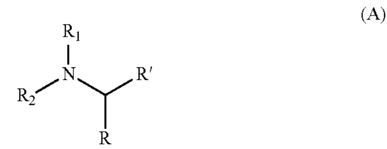

(A)

in which:

$R_1$ represents a hydroxyalkyl radical, the alkyl part being linear and containing two carbon atoms;

$R_2$ is chosen from a hydrogen atom and a linear alkyl radical containing two carbon atoms and substituted with one or more hydroxyl (—OH) radicals;

R and R', which may be identical or different, are each chosen from a hydrogen atom, an alkyl, hydroxyalkyl, alkoxy, alkylamino, dialkylamino or alkoxyalkyl radical, where alkyl is a linear or branched hydrocarbon-based chain containing from 1 to 10 carbon atoms, preferably from 1 to 6 carbon atoms, and a cycloalkyl radical containing from 3 to 9 carbon atoms, with the restriction that R and R' cannot each simultaneously represent a hydrogen atom; or else R and R' together form, with the carbon atom which bears them, a saturated or totally or partially unsaturated, mono-, bi- or polycyclic radical optionally comprising one or more heteroatoms chosen from oxygen, sulfur and nitrogen, said process comprising a step of reductive amination, in the presence of hydrogen and a catalyst, of a carbonyl compound of formula (1) with a hydroxyalkylamine of formula (2):

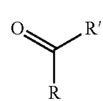

(1)

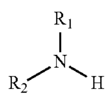

(2)

in which R, R', $R_1$ and $R_2$ are as defined above.

In the present description, and unless otherwise indicated, the term alkyl radical is intended to mean: a linear or branched, optionally substituted, hydrocarbon-based radical containing from 1 to 10 carbon atoms, preferably from 1 to 6 carbon atoms, or a cyclic hydrocarbon-based radical containing from 3 to 9 carbon atoms, preferably from 5 to 9 carbon atoms;

the term mono-, bi- or polycyclic radical is intended to mean: a saturated or totally or partially unsaturated, optionally substituted, mono-, bi- or polycyclic radical optionally comprising one or more heteroatoms chosen from oxygen, sulfur and nitrogen, with a number of ring members of between 3 and 12. Preferably, said radical is monocyclic and comprises from 3 to 9 ring members, preferably it comprises 5, 6 or 7 ring members.

In the preferred embodiments of the present invention, the term alkyl is intended to mean: methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, cyclopentylmethyl, n-heptyl, isoheptyl, cyclohexylmethyl, n-octyl, isooctyl, 2-ethylhexyl and n-decyl, preferably methyl, ethyl or propyl;

the term hydroxyalkyl is intended to mean: hydroxymethyl, 1-hydroxyethyl, 2-hydroxyethyl, 1-hydroxy-n-propyl, 2-hydroxy-n-propyl, 3-hydroxy-n-propyl and 1-(hydroxymethyl)ethyl, preferably hydroxyethyl, hydroxypropyl, more preferably 2-hydroxyethyl and 2-hydroxy-n-propyl;

the term alkylamino is intended to mean: methylamino, 2-ethylamino, 1,1-dimethylethyl-2-amino, n-propyl-2-amino, n-propyl-3-amino, n-butyl-4-amino, n-pentyl-5-amino, including arylamino, which is optionally substituted, for example phenylamino;

the term dialkylamino is intended to mean: dimethylamino, di(2-ethyl)amino, di(1,1-dimethylethyl)-2-amino, di(n-propyl)-2-amino, di(n-propyl)-3-amino, di(n-butyl)-4-amino, di(n-pentyl)-5-amino, N-(2-ethyl)-N-methylamino, N-(1,1-dimethylethyl)-N-methyl-2-amino, N-(n-propyl)-N-methyl-2-amino, N-(n-propyl)-N-methyl-3-amino, N-(n-butyl)-N-methyl-4-amino, N-(n-pentyl)-N-methyl-5-amino, N-(2-ethyl)-N-ethylamino, N-(1,1-dimethylethyl)-N-ethyl-2-amino, N-(n-propyl)-N-ethyl-2-amino, N-(n-propyl)-N-ethyl-3-amino, N-(n-butyl)-N-ethyl-4-amino and N-(n-pentyl)-N-ethyl-5-amino, including diarylamino, which is optionally substituted, for example diphenylamino;

the term cycloalkyl is intended to mean: cyclopropyl, cyclobutyl, cyclopentyl, cyclohexyl, cycloheptyl and cyclooctyl, preferably cyclopentyl and cyclohexyl.

Among the compounds of formula (1), preference is given to those chosen from:

ketones: acetone, hydroxyacetone, methyl ethyl ketone (MEK), methyl propyl ketone, methyl isopropyl ketone, methyl isobutyl ketone, diethyl ketone, diisobutyl ketone, tetralone, acetophenone, para-methyl acetophenone, para-methoxy acetophenone, m-methoxy acetophenone, 2-aminoacetophenone, 1-phenyl-3-butanone, cyclobutanone, cyclopentanone, cyclohexanone, benzophenone, 2-aminobenzophenone, 3-aminobenzophenone, 4-aminobenzophenone, 3,3,5-trimethylcyclohexanone, 2,6-dimethylcyclohexanone, cycloheptanone and cyclododecanone;

aldehydes: acetaldehyde, propionaldehyde, n-butyraldehyde, isobutyraldehyde, pivalaldehyde, valeraldehyde, n-hexanal, 2-ethylhexanal, heptanals, in particular n-heptanal, octanals, in particular n-octanal, undecanals, benzaldehyde, para-methoxybenzaldehyde, para-tolualdehyde, phenylacetaldehyde, hydroxypivalaldehyde and furfural.

Among the compounds of formula (2), preference is given to those chosen from primary or secondary hydroxyalkylamines or di(hydroxyalkyl)amines, and in particular those chosen from monoethanolamine and diethanolamine.

The process according to the present invention consists of a reductive amination of aldehydes or of ketones with a monohydroxyalkylamine or a dihydroxyalkylamine, preferably without the addition of organic solvent, performed according to a batch or semi-continuous process, under heterogeneous catalysis (agitated bed of catalyst).

The process according to the present invention is also preferably carried out with a carbonyl compound/amine molar ratio (or MR in the rest of the present disclosure) close to the stoichiometry, more preferably with a slight excess of the carbonyl compound relative to the amine.

Thus, and according to one preferred embodiment of the process according to the present invention, the MR is advantageously between 0.9 and 1.8, preferably between 1.0 and 1.5, for the monoalkylation of primary or secondary amines, and the MR is advantageously between 1.8 and 3.6, preferably between 2.0 and 3.0, more preferably between 2.1 and 2.5, for the dialkylation of primary amines.

This process makes it possible to produce, according to the operating conditions, various alkylalkanolamines, as indicated on the following synthesis schemes, given by way of illustration but which are not limiting in nature, from monoethanolamine (MEoA) and diethanolamine (DEoA):

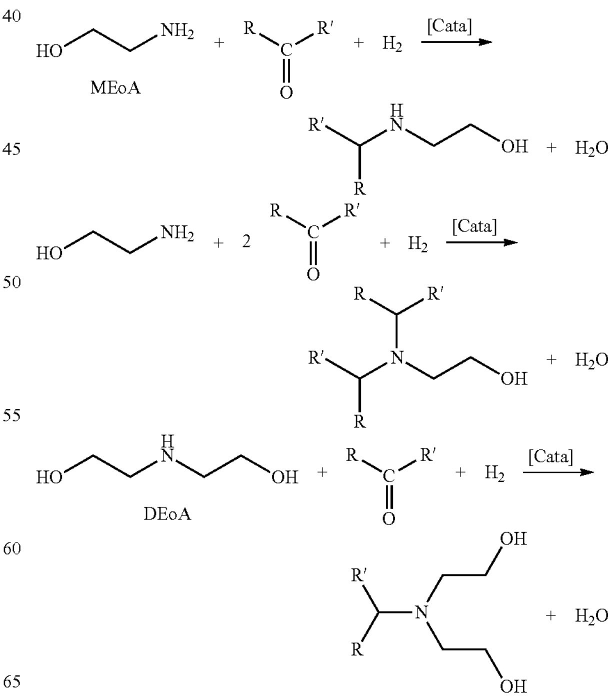

Examples of alkylalkanolamines that can thus be obtained according to the process of the present invention are, in a nonlimiting manner, N-sec-butylethanolamine (sBEA) from methyl ethyl ketone and from monoethanolamine, N-(n-heptyl)diethanolamine (C7DEoA) from n-heptanal and from diethanolamine (DEoA), N-(isopropyl)ethanolamine from acetone and from monoethanolamine (MEoA), N-(n-butyl) diethanolamine from n-butyraldehyde and from diethanolamine (DEoA), and N,N'-di-(n-butyl)ethanolamine from n-butyraldehyde and from monoethanolamine (MEoA).

The hydrogenation catalyst that can be used in the process of the invention may be of any type known to those skilled in the art who are specialists in the field of organic compound hydrogenation. It is preferred to use any type of catalyst normally used for catalytic hydrogenation reactions in a heterogeneous medium.

Nonlimiting examples of such catalysts can be chosen from hydrogenation catalysts based on metals from groups 8, 9, 10 and 11 of the periodic table of elements (IUPAC), preferably Ni-, Co- or Cu-based Raney catalysts, palladium (Pd/C type), and also copper chromites, and more particularly Raney nickel catalysts.

Among the commercially available catalysts suitable for the needs of the process according to the invention, mention may be made, by way of nonlimiting examples, of the nickel catalyst BLM 112 W (Evonik), Amperkat® SK—Ni Fe Cr 4546 (H. C. Starck) and Cu-1955 (BASF Catalysts).

It may be advantageous, or even desirable, to pretreat the catalyst, before using it in the reductive amination reaction according to the invention, said pretreatment consisting of a prior reduction of said catalyst under a hydrogen stream. This is generally the case when the catalyst is sold in its oxidized form (in the case of copper chromites of Cu-1955P type) or only partially reduced form.

Such a pretreatment is recommended, or even essential, when the defined reaction temperature for carrying out the reductive amination according to the invention is below the reduction temperature of said catalyst.

The process according to the present invention is particularly suitable for preparing alkylalkanolamines on the industrial level, in a batch or semi-continuous system, the equipment being similar to that generally used for hydrogenation reactions. Indeed, the process according to the present invention is carried out under a hydrogen pressure, generally of between atmospheric pressure and 150 bar, preferably between 5 bar and 80 bar, and more particularly between 10 bar and 50 bar.

The reaction temperature can vary to large extents depending on the nature of the raw materials and of the catalysts used, and is generally included within a range of from 20° C. to 180° C. For example, the reaction temperature is preferably between 40° C. and 100° C. with Raney nickel catalysts and preferably between 120° C. and 160° C. with copper chromites.

As indicated above, the hydroxylamines of formula 2, and in particular monoethanolamine (MEoA) and diethanolamine (DEoA), are used in anhydrous form or in the form of commercial aqueous solutions. Because of the melting point of anhydrous DEoA, the commercial aqueous form, for example that which has a titer of 85%, is preferred for the needs of the process according to the present invention.

The process according to the invention can be carried out in a batch or semi-continuous system. However, when the carbonyl compound of formula (1) is an aldehyde, the process is advantageously carried out in a semi-continuous system (addition of the aldehyde as it is consumed), in order to control the selectivity.

Preferably, the process according to the invention is carried out without solvent, in particular without organic solvent, it being understood that the amines of formula (2) can be used in an aqueous solution as indicated above.

At the end of the reductive amination reaction, after sedimentation of the catalyst and separation of the liquid crude, the catalyst can be reused as it is for another reductive amination reaction, i.e. another reductive amination reaction according to the invention can be carried out on the same catalyst heel.

Because of the process of the present invention, it is not at all necessary to treat the reaction crude with a reducing agent (such as hydrogen, $NaBH_4$, and the like) in order to inhibit the compounds that may provide a coloration, as is the case in the syntheses conventionally carried out for preparing alkylalkanolamines, in particular those using ethylene oxide.

Thus, the process according to the present invention has the advantage of being able to do without a reducing treatment. The reaction crude is thus directly used in a distillation reaction under reduced pressure, making it possible to obtain colorless alkylalkanolamines of high purity, the coloration of which remains stable during storage.

By way of example, the color of the sBEA obtained according to the process of the present invention is less than 3 Pt—Co units. After 18 months of storage at ambient temperature in glass packaging (in the dark) or HDPE packaging, or 12 months of storage in a steel drum, this lack of color (less than 3 Pt—Co units) persists.

The color is measured using a spectrophotometric method by means of a Dr Lange LTM1 colorimeter according to standard ISO 6271-2: 2004 (platinum-cobalt scale); the color is thus expressed in Pt—Co units (equivalent to Hazen or APHA units which are also often used).

The process for preparing AARs according to the present invention thus makes it possible to be able to have AARs which are colorless or have very little color, whereas, because of their instability, the AAAs currently available on the market are generally sold with specifications of about 50 Hazen, or even 100 Hazen.

The present invention is now illustrated by means of the examples which follow and which have no limiting purpose with regard to the scope of the present invention, said scope being defined, moreover, by means of the appended claims.

EXAMPLE 1

Synthesis of N-(sec-butyl)ethanolamine (sBEA)

N-(sec-butyl)ethanolamine is prepared from methyl ethyl ketone and from monoethanolamine (MEoA), according to the following reaction scheme:

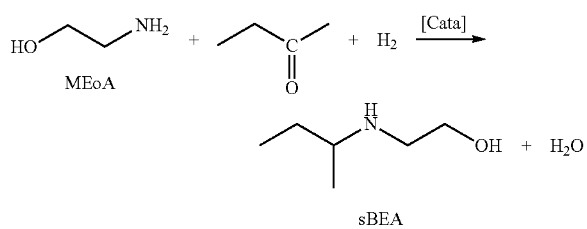

The main side reactions which can occur during this reaction are the following:

a) Hydrogenation of the methyl ethyl ketone to give methyl ethyl carbinol (B2):

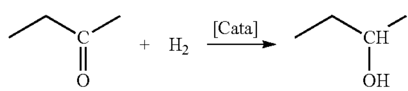

b) Dismutation of the monoethanolamine to give diethanolamine (DEoA) and ammonia:

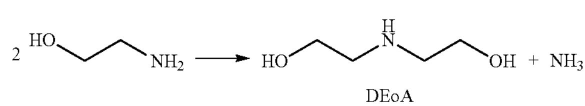

c) Formation of sec-butylamine (B2A) by reductive amination of the methyl ethyl ketone with ammonia:

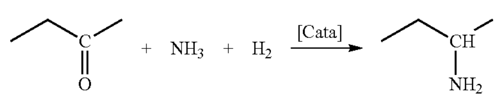

d) Reaction for self-condensation of the methyl ethyl ketone, producing EAK (ethyl amyl ketone) and then EAC (ethyl amyl carbinol):

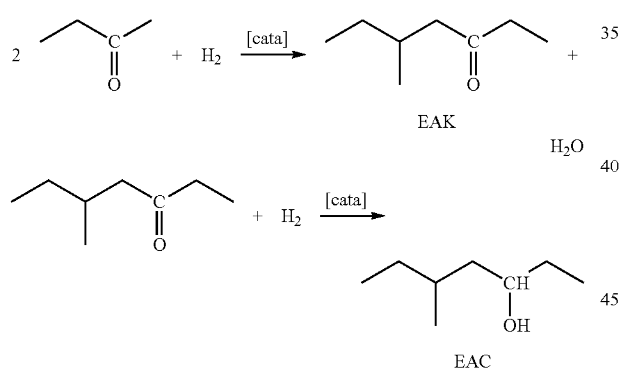

e) Dialkylation of the monoethanolamine corresponding to the reaction of the sBEA with the methyl ethyl ketone:

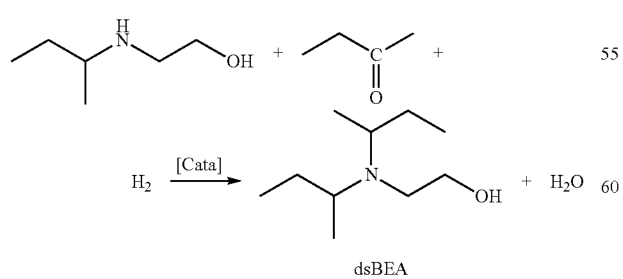

The methyl ethyl ketone (MEK) used (supplier Arkema) has a standard commercial purity of 99.9%.

The monoethanolamine (MEoA) used in its anhydrous form (supplier: BASF) has a purity of greater than 99.7%.

The catalyst used in this example, Cu 1955 P (supplier: BASF Catalysts), is a copper chromite packaged in soluble sachets.

Detailed Procedure

The tests are carried out in a 65 L autoclave equipped with a stirring and gas/liquid dispersion system, with a jacket for heating with steam and cooling with water, with an internal coil for additional cooling of the reaction medium and with pressure and temperature regulators.

Step a): Preliminary Reduction of the Cu 1955P

The Cu 1955P catalyst (2.3 kg in plastic bags of "SecuBag" type) is charged to the autoclave. 34.8 kg of MEK are introduced. The autoclave is flushed with nitrogen, and then nitrogen is injected in order to provide a pressure in the autoclave of approximately 2 bar.

Hydrogen is injected until a pressure of 13 bar is reached at ambient temperature. The stirring and the heating of the autoclave are then begun. When the temperature reaches 80° C., the pressure is increased to 20 bar by injecting hydrogen.

The reduction of the catalyst begins at 125° C. The hydrogen flow rate is limited to 5 $Nm^3/h$. The pressure then decreases to 9 bar. At the end of reduction, the pressure goes back up to 28 bar. The reaction medium is kept for a further 30 min at 130° C. under 28 bar of hydrogen. After the stirring has been stopped and the catalyst has been sedimented, the secondary butanol formed is drained off.

Step b): Synthesis of sBEA

Five successive tests are carried out on the catalyst heel prepared in the previous step (tests A to E). 23 kg of MEK and then approximately 18.4 kg of MEoA are charged. Hydrogen is then injected until a pressure of 15 bar is reached.

The stirring and the heating of the autoclave are then begun. The hydrogenation begins at 80° C. The temperature is increased gradually but in such a way as to maintain an instantaneous maximum flow rate of hydrogen of 5 $Nm^3/h$.

For test A, the hydrogenation is carried out in 5 h 30 min at a temperature of 130° C., under a pressure of 28 bar.

For tests B to D, the hydrogenation is carried out for 3 h 30 min at a maximum temperature of 130° C. and continued for 1 h 30 min at 135° C.

For test E, the hydrogenation is carried out in 5 h 30 min directly at a temperature of 135° C.

For the various tests A to E, at the end of hydrogenation, the reaction medium is cooled to 90° C. and then stirring is stopped. In addition, after hydrogen degassing up to 1 bar, the catalyst is left to sediment for at least 2 hours before the reaction crude is drained off.

Results:

The conversions, selectivities and yields obtained for each of the five tests are collated in table 1 below.

The conversion of MEoA is between 98.6% and 99.8% with an sBEA selectivity with respect to MEoA of between 97.5% and 98.2%, hence a crude molar yield of sBEA relative to the initial MEoA used of about 96% to 98%.

TABLE 1

| | DC | DC | Selectivity/ MeoA (%) | | | Selectivity/MEK (%) | | | | | sBEA/MEoA yield |
|---|---|---|---|---|---|---|---|---|---|---|---|
| Test | MEoA | MEK | B2A | sBEA | DEoA | B2A | B2 | EAK | EAC | sBEA | (%) |
| A | 99.8 | 98.0 | 0.2 | 98.2 | 0.0 | 0.2 | 3.0 | 0.3 | 0.0 | 95.2 | 98.0 |
| B | 99.8 | 98.0 | 0.2 | 98.2 | 0.0 | 0.2 | 3.6 | 0.4 | 0.0 | 94.3 | 98.0 |
| C | 98.6 | 98.0 | 0.2 | 98.2 | 0.1 | 0.2 | 2.7 | 0.3 | 0.0 | 95.4 | 96.8 |
| D | 98.7 | 98.0 | 0.2 | 98.2 | 0.0 | 0.2 | 3.2 | 0.3 | 0.0 | 94.7 | 96.9 |
| E | 99.0 | 96.0 | 0.2 | 97.5 | 0.0 | 0.2 | 3.7 | 0.3 | 0.0 | 93.6 | 96.5 |

The average composition by weight of the crudes of the five operations, determined by gas chromatography, is given in table 2 below:

TABLE 2

| | Concentration (%) |
|---|---|
| $H_2O$ | 12.9 |
| sec-butylamine | 0.11 |
| MEK | 1.30 |
| sec-butanol | 2.50 |
| MEoA | 0.35 |
| EAK | 0.16 |
| EAC | 0.01 |
| sBEA | 81.3 |
| DEoA | 0.02 |
| other organic impurities | 1.35 |

Distillation:

A single distillation operation is carried out on a column of about twenty theoretical plates, using 206 kg of the mixture of the five crudes above.

A preliminary distillation step at atmospheric pressure makes it possible to extract the light products, such as the residual MEK and the B2, and also the majority of the water. The EAK and the EAC forming an azeotrope with the water are also predominantly extracted in this top fraction:

temperature at top of column: 77° C.-99° C.;

temperature in the boiler: 104° C.-155° C.;

reflux ratio at the top of the column ~1.

The distillate is a two-phase distillate. After settling-out of this fraction of light products, 22.7 kg of an aqueous phase (F1 aq.) and 6.0 kg of an organic phase (F2 aq.) of compositions indicated in table 3 below are recovered.

TABLE 3

| Composition by weight | F1 (aq.) 22.7 kg | F1 (org.) 6.0 kg | F2 12.8 kg | 'Pure' fraction 137.7 kg | Final heel 18.4 kg |
|---|---|---|---|---|---|
| B2A | 0.62 | 1.09 | 0.15 | | |
| MEK | 7.63 | 14.30 | 0.32 | | |
| BuOH | 6.95 | 53.75 | 1.28 | | |
| Ethanolamine | — | 0.14 | 5.14 | | 0.08 |
| EAK | 0.18 | 3.00 | 0.25 | | 0.01 |
| EAC | 0.01 | 0.10 | 0.12 | | |
| sBEA | 0.61 | 1.07 | 49.2 | 99.89 | 85.23 |
| Diethanolamine | — | — | — | — | — |
| other organic impurities | 0.69 | 2.75 | 0.83 | 0.09 | 14.66 |
| water | 83.30 | 23.80 | 42.71 | 0.02 | 0.02 |

The distillation is then continued under reduced pressure. The residual water is eliminated at the top of the column and then the 'pure' sBEA is recovered by drawing off via a sidestream at a column height of approximately 70%. The drawing off of the sBEA as pasteurized makes it possible to concentrate the residual MEoA at the top of the column.

pressure at top of column: 60 mbar-70 mbar;

temperature at top of column: 34° C.-100° C.;

temperature at the level of the drawing off via a sidestream: 101° C.-103° C.;

temperature in the boiler: 110° C.-128° C.;

reflux ratio at head of column ~10;

reflux ratio at the level of the drawing off via a sidestream ~1 to 2.

12.8 kg of a fraction F2 and 137.7 kg of 'pure' sBEA having a purity of 99.9%, representing 82.1% of the sBEA present in the initial charge of the boiler, are thus recovered.

Taking into account the "hold-up" of the column, the distillation yield is about 85%.

The high-purity sBEA thus prepared remains virtually colorless (color less than 3 Pt—Co units) after more than 18 months of storage.

EXAMPLE 2

Synthesis of N-(n-heptyl)diethanolamine (C7DEoA)

The n-heptyldiethanolamine is prepared from n-heptanal and diethanolamine (DEoA).

Three synthesis operations (K, L, M) are carried out successively on the same catalyst heel in a 2 L stainless steel Sotelem reactor, using an Amperkat® SK—Ni Fe Cr 4546 Ni/Raney catalyst (supplier H. C. Starck).

Test K

After charging 50 g of Amperkat catalyst to the autoclave (with 95 g of water) and then flushing the autoclave with nitrogen, 391.3 g of 85% DEoA (i.e. 332.6 g net of DEoA corresponding to 3.16 mol) are introduced using a pump.

Hydrogen is then injected until a pressure of 15 bar is reached and then the mixture is heated at 90° C. with stirring and the hydrogen pressure is adjusted to 28 bar.

The heptaldehyde (supplier Arkema, purity 97%) is then introduced using a pump at a flow rate of 350 g/h, while at the same time injecting hydrogen so as to maintain the pressure of 28 bar and while at the same time maintaining the temperature of the reaction medium at 90° C.

After the introduction of 487.5 g of heptaldehyde (i.e. 4.14 mol), the reaction medium is kept stirring at 90° C. and under 28 bar of hydrogen for a further 30 minutes.

The stirring is then stopped and the catalyst is left to sediment for at least two hours, after hydrogen degassing up to 1 bar.

The supernatant liquid reaction crude is then drawn off via a filter (to remove the possible catalyst fines). 866.6 g of crude C7DEoA are thus recovered, the composition by weight of which, determined by gas chromatography (table 4), indicates a total absence of residual heptaldehyde, the excess heptaldehyde relative to the DEoA being mostly converted to n-heptanol.

Test L

The test is carried out according to the same procedure as for test K, but by directly charging 395 g of 85% DEoA (i.e. 335.8 g net of DEoA corresponding to 3.19 mol) to the catalyst heel of test K kept in the autoclave and by injecting an amount of 432.3 g (3.67 mol) of heptaldehyde over the course of 1 hour 15 minutes. At the end of the reaction, 833.3 g of crude C7DEoA are thus recovered, the composition by weight of which, determined by gas chromatography, is indicated in table 4.

Test M

The test is carried out according to the same procedure as for test K, but by directly charging 401.1 g of 85% DEoA (i.e. 340.9 g net of DEoA corresponding to 3.24 mol) to the catalyst heel of test L kept in the autoclave and by injecting an amount of 432.7 g (3.68 mol) of heptaldehyde over the course of 1 hour 15 minutes. At the end of the reaction, 837.3 g of crude C7DEoA are thus recovered, the composition by weight of which, determined by gas chromatography, is indicated in table 4.

TABLE 4

| | Composition by weight of the reaction crudes (%) | | | | | |
|---|---|---|---|---|---|---|
| Test | $H_2O$ | Heptaldehyde | Heptanol | DEoA | C7DEoA | other impurities |
| K | 20 | — | 13.6 | 0.7 | 63.3 | 2.4 |
| L | 13.5 | — | 9.3 | 1.7 | 73.7 | 1.8 |
| M | 13.5 | — | 8.6 | 1.8 | 74.0 | 2.2 |

| Test | Conversion of DEoA (%) | C7DEoA selectivity with respect to DEoA (%) | C7DEoA selectivity with respect to heptaldehyde (%) | Heptanol selectivity with respect to heptaldehyde (%) | Molar yield of C7DEoA relative to the DEoA used (%) |
|---|---|---|---|---|---|
| K | 98.0 | 96.3 | 70.7 | 26.6 | 94.4 |
| L | 95.3 | 99.4 | 81.9 | 17.9 | 95.5 |
| M | 95.2 | 98.4 | 82.2 | 16.6 | 94.9 |

After mixing of the three reaction crudes above, a purification operation is carried out on a Sovirel distillation column packed with Multiknit packing with a height of 1 m.

After charging to the boiler of the column 2113 g of the crude C7DEoA mixture, the latter is concentrated by azeotropic extraction of the heptanol and of the water at atmospheric pressure (temperature at top: 96-98° C.) and then depletion of the water under a pressure of 50 mbar with a maximum temperature in the boiler at the end of concentration of 150° C.

243.2 g of an organic fraction comprising 86.2% of heptanol, 5.2% of water and 7.6% of organic impurities and then 312.7 g of an aqueous phase comprising 99.5% of water, 0.25% of heptanol and 0.25% of organic impurities are thus recovered.

The composition of the heel (1509.3 g) after concentration is the following:

Heptanol: 0.09%;
DEoA: 1.86%;
Other organic impurities: 1.60%;
Water: 0.06%;
C7DEoA: 96.4%.

By continuing the fractional distillation of this heel in the same apparatus, under a pressure of less than 1 mbar and after separation of a DEoA-rich top fraction, 1358 g of distilled C7DEoA are obtained at a temperature at the top of the column of 137.0° C.-137.5° C. and with a maximum temperature in the boiler of 180° C.

The purity of this distilled C7DEoA is 98.7%, with a residual DEoA content of 0.05%, a water content of 0.02% and a color of less than 3 Pt—Co units.

With a distillation yield of 89.5%, the overall molar yield of distilled C7DEoA is therefore about 85% relative to the DEoA initially processed.

After 6 months of storage in a glass bottle, at ambient temperature and in the dark, the color of the C7DEoA thus prepared remains quasi-stable since it is equal to only 5 Pt—Co units.

The following examples are carried out according to similar procedures, with the raw materials being varied as indicated.

EXAMPLE 3

Synthesis of N-(isopropyl)ethanolamine (IPAE) from Acetone and MEoA According to a Batch Process (sBEA Type)

With an acetone/MEoA molar ratio of 1.05, an amount by weight of Cu 1955P catalyst of 11% relative to the acetone, a reaction temperature of 110° C. and under a hydrogen pressure of 28 bar, total conversion of the acetone is obtained. The conversion of the MEoA is 99.7% with an N-(isopropyl) ethanolamine selectivity of 98.5%, i.e. a crude molar yield of IPAE of 98.2% relative to the MEoA processed.

EXAMPLE 4

Synthesis of N-(n-butyl)diethanolamine (BDEoA) from n-butyraldehyde and 85% DEoA According to a Semi-Continuous Process (C7DEoA Type)

With an n-butyraldehyde/DEoA molar ratio of 1.04, an amount by weight of Amperkat® SK—NiFeCr 4546 catalyst of 7.3% relative to the DEoA, and a semi-continuous introduction of the n-butyraldehyde over the course of 1 hour 15 minutes, while maintaining the reaction temperature at 65° C.-70° C., under a hydrogen pressure of 28 bar, complete conversion of the N-butyraldehyde is obtained. The conversion of the DeoA is 94% with an N-(n-butyl)diethanolamine selectivity of 98.3%, hence a crude molar yield of BDEoA of 92.4% relative to the DEoA processed.

The BDAoE is extracted, by fractional distillation of the reaction crude, under a pressure of 25 mbar and at a temperature at the top of the column of 145° C.-146° C. The purity of the BDEoA is 99.2% with a distillation yield of 91%. The color of the BDEoA thus prepared is less than 3 Pt—Co units on leaving the distillation, and 25 Pt—Co units after 18 months of storage in a glass bottle at ambient temperature and in the dark.

EXAMPLE 5

Synthesis of N,N'-di-(n-butyl)ethanolamine (DBEoA) from n-butyraldehyde and MEoA According to a Semi-Continuous Process (C7DEoA Type)

With a butyraldehyde/MEoA molar ratio of 2.16, an amount by weight of Amperkat SK—NiFeCr 4546 catalyst of 10.6% relative to the MEoA, and a semi-continuous introduction of the butyraldehyde over the course of 1 hour 50 minutes, while maintaining the reaction temperature at 70° C., under a hydrogen pressure of 28 bar, complete conversion of the butyraldehyde and of the MEoA is obtained. The crude molar yield of DBEoA is 79% relative to the MEoA processed; the two main by-products are N-(n-butyl)ethanolamine and n-butanol.

The DBEoA is extracted, by fractional distillation of the reaction crude, under a pressure of 46 mbar and at a temperature at the top of the column of 130.5° C. The purity of the DBEoA is 99.8% with a distillation yield of 86% and a color of less than 3 Pt—Co units.

The invention claimed is:

1. A process for preparing alkylalkanolamines of formula (A):

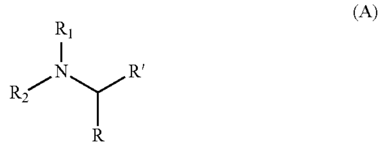

wherein:

$R_1$ represents a hydroxyalkyl radical, the alkyl part being linear and containing two carbon atoms;

$R_2$ is chosen from a hydrogen atom and a linear alkyl radical containing two carbon atoms and substituted with one or more hydroxyl (—OH) radicals;

R and R', which may be identical or different, are each chosen from a hydrogen atom, an alkyl, hydroxyalkyl, alkoxy, alkylamino, dialkylamino or alkoxyalkyl radical, where alkyl is a linear or branched hydrocarbon-based chain containing from 1 to 10 carbon atoms, and a cycloalkyl radical containing from 3 to 9 carbon atoms, with the restriction that R and R' cannot each simultaneously represent a hydrogen atom;

or else

R and R' together form, with the carbon atom which bears them, a saturated or totally or partially unsaturated mono-, bi- or polycyclic radical optionally comprising one or more heteroatoms chosen from oxygen, sulfur and nitrogen, said process comprising a step of reductive amination, in the presence of hydrogen and a catalyst, of a carbonyl compound of formula (1) with a hydroxyalkylamine of formula (2):

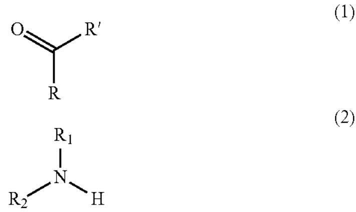

in which R, R', $R_1$ and $R_2$ are as defined above, wherein the hydroxyalkylamine of formula (2) is in aqueous solution, and wherein water is formed during and remains present during the reductive amination, and thereby the step of reductive amination is carried out in the presence of water and without a water segregating agent.

2. The process as claimed in claim 1, wherein the compound of formula (1) is selected from the group consisting of acetone, hydroxyacetone, methyl ethyl ketone (MEK), methyl propyl ketone, methyl isopropyl ketone, methyl isobutyl ketone, diethyl ketone, diisobutyl ketone, tetralone, acetophenone, para-methyl acetophenone, para-methoxy acetophenone, m-methoxy acetophenone, 2-amino acetophenone, 1-phenyl-3-butanone, cyclobutanone, cyclopentanone, cyclohexanone, benzophenone, 2-aminobenzophenone, 3-aminobenzophenone, 4-aminobenzophenone, 3,3,5-trimethylcyclohexanone, 2,6-dimethylcyclohexanone, cycloheptanone, cyclododecanone, acetaldehyde, propionaldehyde, n-butyraldehyde, isobutyraldehyde, pivalaldehyde, valeraldehyde, n-hexanal, 2-ethylhexanal, heptanals, octanals, undecanals, benzaldehyde, para-methoxybenzaldehyde, para-tolualdehyde, phenylacetaldehyde, hydroxypivalaldehyde, and furfural.

3. The process as claimed in claim 1, wherein the compound of formula (2) is chosen from monoethanolamine and diethanolamine.

4. The process as claimed in claim 1, wherein the compound of formula (A) is N-sec-butylethanolamine (sBEA), obtained from methyl ethyl ketone and from monoethanolamine, N-(n-heptyl)diethanolamine (C7DEoA) obtained from n-heptanal and from diethanolamine (DEoA), N-(isopropyl) ethanolamine obtained from acetone and from monoethanolamine (MEoA), N-(n-butyl)diethanolamine obtained from n-butyraldehyde and from diethanolamine (DEoA), and N,N'-di-(n-butyl)ethanolamine obtained from n-butyraldehyde and from monoethanolamine (MEoA).

5. The process as claimed in claim 1, wherein the catalyst is chosen from hydrogenation catalysts based on metals of groups 8, 9, 10 and 11 of the periodic table of elements (IUPAC).

6. The process as claimed in claim 1, wherein the hydrogen pressure is between atmospheric pressure and 150 bar.

7. The process as claimed in claim 1, wherein the reaction temperature is included in a range of from 20° C. to 180° C.

8. The process as claimed in claim 1, which is carried out in a batch or semi-continuous system.

9. The process as claimed in claim 1, wherein the reaction crude is used in a distillation operation.

10. The process as claimed in claim 1, wherein it is carried out without organic solvent.

11. The process of claim 1, wherein the alkyl is a linear or branched hydrocarbon-based chain containing from 1 to 6 carbon atoms.

12. The process of claim 2, wherein the heptanal is n-heptanal.

13. The process of claim 2, wherein the octanal is n-octanal.

14. The process of claim 5, wherein the hydrogenation catalyst is a Ni-based, Co-based or Cu-based Raney catalyst, palladium (Pd/C type), or copper chromite.

15. The process of claim 14, wherein the hydrogenation catalyst is a Raney nickel catalyst.

16. The process of claim 6, wherein the hydrogen pressure is between 5 bar and 80 bar.

17. The process of claim 16, wherein the hydrogen pressure is between 10 bar and 50 bar.

18. The process of claim 8, wherein the process is carried out in a semi-continuous system when the carbonyl compound of formula (1) is an aldehyde.

* * * * *